United States Patent [19]

Haselbeck et al.

[11] Patent Number: 5,179,004
[45] Date of Patent: Jan. 12, 1993

[54] PROCESS FOR THE DETECTION OF COMPOUNDS CONTAINING CARBOHYDRATE AND A SUITABLE REAGENT THEREFOR

[75] Inventors: Anton Haselbeck, Weilheim; Wolfgang Hösel, Tutzing; Herbert von der Eltz, Weilheim; Edith Schickaneder, Munich, all of Fed. Rep. of Germany

[73] Assignee: Boehringer Mannheim GmbH, Mannheim, Fed. Rep. of Germany

[21] Appl. No.: 454,189

[22] Filed: Dec. 21, 1989

[30] Foreign Application Priority Data

Dec. 23, 1988 [DE] Fed. Rep. of Germany ....... 3843598
Jan. 11, 1989 [DE] Fed. Rep. of Germany ....... 3900639

[51] Int. Cl.⁵ .................... G01N 33/66; G01N 33/536
[52] U.S. Cl. .................................. 435/7.92; 435/7.9; 435/7.94; 435/961; 436/501; 436/536; 436/543
[58] Field of Search .................. 435/7.94, 7.9, 7.92, 435/961; 436/501, 536, 543

[56] References Cited

U.S. PATENT DOCUMENTS

| | | | |
|---|---|---|---|
| 4,289,747 | 9/1981 | Chu | 435/7.8 |
| 4,371,515 | 2/1983 | Chu | 435/7.8 |
| 4,526,871 | 7/1985 | Avrameas et al. | 436/504 |
| 4,762,781 | 8/1988 | Geffard | 435/7 |
| 4,767,720 | 8/1988 | Lingwood | 436/536 |
| 4,786,594 | 11/1988 | Khanna et al. | 435/6 X |
| 4,837,395 | 6/1989 | Leeder et al. | 435/7.8 |
| 4,874,813 | 10/1989 | O'Shannessy | 530/816 |
| 4,886,761 | 12/1989 | Gustafson et al. | 436/518 |
| 4,959,307 | 9/1990 | Olson | 436/501 X |

FOREIGN PATENT DOCUMENTS

| | | |
|---|---|---|
| 0166623 | 1/1986 | European Pat. Off. |
| 0171243 | 2/1986 | European Pat. Off. |
| 0218347 | 4/1987 | European Pat. Off. |
| 2296 | 10/1980 | World Int. Prop. O. |

OTHER PUBLICATIONS

A. Haselbeck et al., Glycobiology, UCLA Symposia on Molecular and Cellular Biology, Jan. 14–20, 1989, Frisco, CO, application of a new carbohydrate detection system to the characterization of recombinant glycoproteins.

O'Shannessy et al., Anal. Biochem. 163: 204–209 (1987).
Volz et al., Hist. J. 19:318 (1987).

Primary Examiner—Mary E. Ceperley
Attorney, Agent, or Firm—Felfe & Lynch

[57] ABSTRACT

For the detection of compounds containing carbohydrate the compound to be detected is reacted with a conjugate which contains a group which enables a specific binding to the substance to be detected and contains a hapten with a molecular weight from 300 to 1200, afterwards the complex formed is brought into contact with labelled antibodies directed against the hapten and the label is determined in a known way.

15 Claims, No Drawings

PROCESS FOR THE DETECTION OF COMPOUNDS CONTAINING CARBOHYDRATE AND A SUITABLE REAGENT THEREFOR

The invention concerns a process for the detection of compounds containing carbohydrate, as well as a suitable reagent therefor.

Compounds containing carbohydrate are widespread. Besides derivatives of glycerol such as e.g. monoglycerides, which are e.g. used as emulgators and are present in foods, the sugars are, above all, ubiquitous, in particular the pentoses and hexoses as well as their derivatives. The sugars occur in the organism in many variations in particular also in the form of glycoconjugates such as e.g. glycoproteins. Very many active substances can only be transported in the organism or are only effective when present in a glycosylated form. It is therefore desirable to be able to detect such compounds with great accuracy from sample solutions as well as on tissue sections quantitatively as well as qualitatively. Furthermore, it is important to be able to distinguish the individual sugars or compounds containing OH-groups from one another.

Many processes are already known by which compounds containing carbohydrate can be detected quantitatively as well as qualitatively with chemical or biochemical methods. Thus it is known for example that a mixture of sugars can be separated chromatographically or electrophoretically and afterwards the individual sugars can be visualized by staining. Suitable, for example, are the reaction with phenol-sulphuric acid, the reaction with periodate and subsequent staining with Schiff's reagent or silver or subsequent dansyl-fluorimetric determination. A disadvantage of these chemical methods is that they are either not very specific or else they are too insensitive. On the other hand, the more sensitive chemical methods have the disadvantage that they are very complicated to carry out and very susceptible to interference.

Furthermore, it was known for example from DE-OS 36 29 194 that glyco-residues in conjugates can be detected by reaction with a biotin derivative followed by reaction with a labelled streptavidin. However, a disadvantage of this procedure is that the method is not very sensitive because of a high background.

The object of the present invention was therefore to provide a process by which compounds containing carbohydrate can be detected sensitively and specifically as well as qualitatively and quantitatively. Furthermore a process should be developed which is easy to carry out and offers a wide range of applications.

This object is achieved by a process for the detection of compounds containing carbohydrate which is characterized in that the compound to be detected is reacted with a compound (denoted subsequently as conjugate) which contains a group which enables a specific binding to the carbohydrate part of the substance to be detected and contains a hapten with a molecular weight from 300-1200, afterwards the complex formed is brought into contact with labelled antibodies directed against the hapten and the label is determined in a known way.

Surprisingly it was found that with the process according to the present invention compounds containing carbohydrate can be detected very sensitively. The process is suitable for staining on chromatograms and tissue sections as well as for the quantitative estimation. Although the binding constant of the biotin/avidin interaction at $K=10^{15}$ mol$^{-1}$ is at least a factor $10^5$ higher than the binding constant of the interaction of haptens with the corresponding antibodies which are in the range of $K=2\times10^8$ mol$^{-1}$ to $7\times10^9$ mol$^{-1}$ and in addition the biotin/avidin interaction is favoured because there are four biotin binding sites in the avidin molecule, the process according to the present invention allows a detection sensitivity which is at least as great as the detection sensitivity of the biotin/avidin system. A further surprising advantage is that there is practically no background when using the haptens and the corresponding antibodies. In addition the process can be carried out simply and reproducibly.

The process according to the present invention is suitable for the detection of compounds containing carbohydrate. It is particularly suitable for the detection of hexoses, pentoses and sialic acid, their derivatives as well as substances containing sugars (glycoconjugates) such as e.g. the glycoproteins. The process according to the present invention can be varied in clinical, biochemical and food chemical diagnostics in such a way that the total content of sugars as well as the individual compounds in a mixture can be detected.

The compounds can be detected in solution (preferably with an ELISA-test) as well as bound to a carrier. The process according to the present invention is particularly suitable for all glycoconjugates present in a fixed form either on a carrier or in a tissue.

The glycoproteins can even be detected directly in the gel which serves to separate the mixture. It is however preferable first to transfer the separated mixture on to a carrier and afterwards to detect the desired compound.

To carry out the process according to the present invention the compound to be detected is first reacted with a conjugate which contains a group that enables a specific binding to the substance to be detected and contains a hapten with a molecular weight between 300 and 1200.

The group is chosen according to how specific the detection should be. Substances are suitable which on the one hand react specifically with the compound to be detected in an unchanged form. For this lectins or carbohydrate-specific antibodies (Biochem. I. 245, (1987) 1-11) are taken above all into consideration. Different lectins are known which bind specifically to the individual types of sugar (Ann.Rev.Biochem. 55 (1986) 35-67). These lectins can be isolated from plants and are available commercially. The following can for example be used: peanut-agglutinin (PNA) which binds specifically to terminally-bound galactose residues, wheat germ agglutinin (WGA) which is specific for N-acetylglucosamine, Galanthus nivalis agglutinin (GNA) which binds specifically to terminally-bound mannose residues, Sambucus nigra agglutinin (SNA) which is specific for 2-6 bound sialic acids as well as Maackia amurensis lectin (MAL) which binds specifically to 2-3 bound sialic acids. The expert can therefore easily find the lectin suitable for the respective purpose. Antibodies or their fragments which react specifically with the substance to be detected are suitable as antibodies. A further possibility is to specifically oxidize the compound to be detected and then to use as the group a functional group which reacts with the specifically oxidized residues formed, as a rule an aldehyde or carboxyl group.

The pretreatment can be carried out for this in a known way. It is preferable to oxidize the carbohydrate part of the compound to be detected with a specific enzyme or with periodate. In this process aldehyde groups are formed. Amines or hydrazines are suitable as the functional groups which are capable of binding thereto.

In a particular embodiment the compound to be detected is therefore reacted with a conjugate which contains an amine or hydrazide moiety. After this reaction it is particularly preferable in the case of the amine to also dehydrogenate the Schiff's bases which form in this process in order to convert the unstable aldimine bond into a stable amine bond.

The oxidation of the carbohydrate moiety is carried out under known conditions. If a specific enzyme (e.g. galactose oxidase or glucose oxidase) is used the most favourable conditions are chosen for the enzyme activity. The conditions for the oxidation with periodic acid are also known. As a rule the oxidation is carried out for ca. 10 to 30 minutes at room temperature with 5 to 15 mmol/l periodate. If an individual compound has to be specifically detected the oxidation conditions are adjusted in such a way that only the desired compound is oxidized. In this process milder conditions can also be appropriate according to the compound to be treated. Following the periodate oxidation it is expedient to destroy excess periodate still present in the solution by the addition of bisulphite.

The second component of the conjugate is a hapten with a molecular weight from 300–1200. This hapten serves to specifically bind a label. Suitable for this are for example steroids (such as e.g. digoxin, digoxigenin, cortisol, oestriol, oestradiol, theophyllin, testosterol, bile acids, progesterone and aldosterone); short chain peptides (such as e.g. argipressin, oxytocin and bradykinin); fluorescein and its derivatives; $T_3$, $T_4$, aflatoxin, atrazine, plant hormones such as e.g. gibberillins; and alkaloids (such as e.g. reserpine and ajmalicin). It is preferable to use a hapten which does not occur endogeneously in the organism from which the respective sample originates. In particular haptens which do not occur naturally such as e.g. anellated aromatic hydrocarbons are used.

It is particularly preferably to use digoxin, digoxigenin, fluorescein and derivatives as well as theophyllin as the hapten.

The hapten can be bound directly to the group which mediates the specific binding. However, the hapten is preferably bound to the group via a spacer. For this the spacer should have a length in the range of 3 to 32 atoms. It is usually made up of molecules containing the atoms C, O, S or/and N.

In a preferred embodiment of the invention the steroid hapten is bound via a spacer of 3 to 16 atoms length. It is especially preferred to use a spacer with a length of 3 to 9 atoms for lectins and a spacer with a length of 9 to 16 atoms for amines or hydrazides. N-acyl-ε-aminocaproic acids are preferably used as the spacer. Especially preferred are N-acetyl-ε-aminocaproic acid and N-succinyl-ε-aminocaproic acid.

After carrying out the first step of the procedure according to the present invention a complex forms of the compound to be detected and conjugate. If a separation is to be carried out by chromatography especially gel chromatography or gel electrophoresis this can take place either before or after the formation of the complex. This depends on the substance to be detected. The conjugate used according to the present invention has a relatively low molecular weight so that it does not impair a separation by SDS-gel electrophoresis when the compound to be detected is a macromolecular substance such as for example a glycoprotein. In this case the reaction with the conjugate can therefore be carried out first and afterwards the separation in the gel. The detection can then be carried out directly in the gel. It is preferable to transfer the separated fractions by blotting on a membrane (e.g. nitrocellulose filter, nylon or polyvinyl membrane) and visualize them there. The separation can also be carried out first, especially when the compounds to be detected have a relatively low molecular weight, followed by reaction with the conjugate according to the present invention and detection of the label. Thus, for example, a sugar mixture can first be separated chromatographically and afterwards detected by reaction with the conjugate according to the present invention and with the corresponding labelled antibody. The method suitable for each case depends on the substance to be detected and can be easily determined for a special case.

The complex formed from the substance to be detected and the conjugate is reacted afterwards with a labelled antibody directed against the hapten. Monoclonal or polyclonal antibodies or their fragments and derivatives can be used as antibodies. Such antibodies are known to the expert.

The labelling of the antibody is carried out in a well known way. Suitable are e.g. labelling with an enzyme, radioactive labelling, labelling with a bioluminescent or chemiluminescent compound or a fluorescent compound, or with a compound which results in such a signal by indirect means. It is preferable to use an enzyme as the label. The use of alkaline phosphatase, peroxidase or β-galactosidase as the enzyme is especially preferred. In particular the labelled enzyme alkaline phosphatase is preferred when carrying out the procedure according to the present invention. The determination of the label is carried out in a well known way. When using an enzyme as label a substrate has to be added for detection which gives a detectable reaction. For this, it is preferable to use leuco systems especially indigoid systems as oxidizable compounds and tetrazolium salts as oxidizing agents. Especially preferred is a redox system consisting of 5-bromo-4-chloro-3-indolylphosphate (X-phosphate) and nitroblue-tetrazolium. In this process alkaline phosphatase cleaves the X-phosphate which forms a blue, sparingly soluble dimer by cleavage of the phosphate and oxidation, whereby at the same time the tetrazolium compound is reduced to a likewise blue and sparingly soluble formazan.

A further possibility for the labelling is to label with gold which is especially suitable for the detection in tissue sections.

Before reaction with the anti-hapten antibody it is preferable to treat with a reagent which binds to the reactive parts of the carrier as well as of the other components of the mixture. Casein is for example suitable for this.

The detection limit for the individual glycoproteins depends on the type of the various glycoproteins. The sensitivity of the procedure according to the present invention is however very high and glycoproteins can be detected down into a range of 10 ng. Furthermore, various sugar residues can be distinguished by the procedure according to the present invention. Thus e.g. by variation of the oxidation conditions glycoproteins containing sialic acid can be distinguished from asialo compounds. For this the oxidation is carried out with periodate under very mild conditions at 0° C. in which the sialic acids are only just oxidized but not, however, the asialo compounds. In the same way according to the present invention sugars bound by an O-glycosidic bond can be distinguished from those bound by a N-glycosidic bond in that the mixture to be assayed is first treated with N-glycosidase and afterwards it is separated according to its molecular weight. A positive sugar reaction of a conjugate indicates an O-glycosidic bond.

The presence of detergents when carrying out the process according to the present invention does not interfere.

A further embodiment of the present invention is a reagent for the detection of compounds containing carbohydrate according to the above mentioned procedure which is characterized in that it contains a conjugate of a hapten with a molecular weight of 300–1200 and of a group specifically bindable to the substance to be detected as well as a labelled anti-hapten antibody which is physically separated from it.

When a radioactive or fluorescent substance or gold is used as the label for the anti-hapten antibody, this reagent is sufficient to visualize the label. If an enzyme is used as the label the reagent according to the present invention contains preferably in addition a detection system which is a substrate for this enzyme that forms a detectable product by reaction with the enzyme.

The reagent is stable for a very long time when stored properly and gives reproducible values even after storage for several months.

The invention is elucidated by the following Examples.

EXAMPLE 1

Digoxigenin-O-succinyl-ε-amidocaproic acid-(N-tert.-butyloxycarbonyl)-hydrazide 1.40 g (2 mmol) digoxigenin-O-succinyl-ε-amidocaproic acid-N-hydroxy-succinimide ester prepared according to the procedure described in DE-A 3,800,644, 0.29 g (2.2 mmol) t-butyloxycarbonyl-hydrazide and 0.29 ml (2.1 mmol) triethylamine are stirred in 8 ml dioxan for 20 hours at room temperature and humidity was excluded. After removal of the solvent by distillation in a vacuum 100 ml ice water is added to the resinous residue and left standing for 4 hours. During this period the product crystallizes. After aspiration, it is washed with ice water and dried over $CaCl_2$ in a vacuum.

Yield 1.23 g (86% of the theoretical yield),
MW: 717.9 colourless powder, melting point 160° C.
TLC: silica gel, nitromethane/methanol 8:2, $R_f=0.32$

EXAMPLE 2

Digoxigenin-O-succinyl-ε-amidocaproic acid-hydrazidehydrochloride 1.10 g (1.5 mmol) of the tert.-butyloxycarbonyl protected product is dissolved in 6 ml trifluoroacetic acid and diluted with 6 ml $CH_2Cl_2$. After stirring for one hour at room temperature all volatile components are extracted in a vacuum at 40° C. and twice distilled azeotropically with 5 ml dioxan. The colourless resin thus obtained is then taken up in 30 ml 50% methanol, filtered and chromatographed on 200 ml DEAE-Sephadex/Cl$^-$ with 50% methanol. The first fraction yields the desired product after lyophilization.

Yield: 0.69 g (70% of the theoretical yield) colourless powder
TLC: silica gel, nitromethane/methanol 8:2, $R_f=0.14$
MW: 653.2

EXAMPLE 3

Digoxigenin-3-carboxymethyl ether-ε-amidocaproic acid-(N-tert.-butyloxycarbonyl)-hydrazide 1.32 g (2 mmol) digoxigenin-3-carboxymethyl ether-ε-amidocaproic acid-N-hydroxysuccinimide ester (preparation according to DE-A 3,836,656), 0.29 g (2.2 mmol) t-butyloxycarbonyl-hydrazine and 0.29 ml (2.1 mmol) triethylamine are reacted and processed as described in Example 1.

Yield: 1.17 g (89% of the theoretical yield)
MW: 691.5 colourless powder

EXAMPLE 4

Digoxigenin-3-carboxymethyl ether-ε-amidocaproic acid-hydrazide-hydrochloride 1.04 g (1.5 mmol) of the tert.-butyloxycarbonyl protected product obtained previously is reacted as described in Example 2.

Yield: 0.76 g (81% of the theoretical yield)
MW: 627.8

EXAMPLE 5

Preparation of Lectin Conjugated with Digoxigenin $1 \times 10^{-3}$ mmol/l lectin is dissolved in 10 ml 0.05 mol/l phosphate buffer, pH 8.5. $4 \times 10^{-3}$ mmol/l (=2.8 mg) digoxigenin-O-succinyl-amidocaproic acid-O-succinimide ester (preparation according to DE-A 38 00 644) is dissolved in 500 μl dimethyl formamide p.A. and added to the lectin solution.

The reaction is allowed to proceed for 4 hours at 25° C. and shaken from time to time. Then the reaction solution is dialysed for 48 hours at 4° C. against 1 l portions of distilled $H_2O$, during which the water is renewed at least twice.

The dialysed solution is lyophilized.
Yield: 90 to 100%

EXAMPLE 6

Detection of Glycan Structures in Tissue Sections

It is carried out essentially as described in C.F.A. Culling, R. T. Allison and W. T. Barr, Cellular Pathology Technique, pages 219 to 224, Butterworths London, 4th Edition 1985.

Accordingly paraffin sections are fixed in xylol and the descending series of alcohols, rinsed in distilled water and oxidized for 30 min in a 1% periodate solution. After washing in distilled water the section which is on a slide is overlayed with 0.1 mol/l sodium acetate buffer, pH 5.5, 10 mmol/l digoxigenin-O-succinyl-ε-amidocaproic acid-hydrazide-hydrochloride (Example 2) or digoxigenin-3-carboxymethyl ether-ε-amidocaproic acid-hydrazide-hydrochloride (Example 4) and brought into reaction for 1 to 2 hours in a humid chamber.

After washing three times with TBS (50 mmol/l Tris HCl pH 7.5, 150 mmol/l NaCl) incubation with the antibody follows: normally a 1:100 to 1:1000 dilution in TBS is applied to the section (ca. 50 to 100 μl) and the section is incubated in a humid chamber for about 30 to 60 minutes.

After washing three times with TBS the alkaline phosphatase reaction takes place by immersion of the sections in 0.1 mol/l Tris-HCl, pH 9.5, 0.1 mol/l sodium chloride, 0.05 mol/l magnesium chloride and 5-bromo-4-chloro-3-indolyl-phosphate (37.5 μl/10 ml; stock solution 50 mg/ml in dimethyl formamide) and nitrotetrazolium blue (NBT) (50 μl/10 ml; stock solution 75 mg/ml in 70% dimethyl formamide).

The colour development is followed under the microscope and is usually at its optimum after a few minutes. In order to stop the reaction the section is rinsed in distilled water and embedded.

EXAMPLE 7

Detection of Glycoproteins by Blotting on Nitrocellulose Membranes with Lectins Conjugated with Digoxigenin A solution containing glycoproteins is separated in the usual way by electrophoresis on SDS-PAGE. After the separation the fractions are transferred on to nitrocellulose membranes by blotting (Schleicher and Schüll BA85).

After the transfer the nitrocellulose is specifically stained for protein using Ponceau S. For this the blot is incubated for 5 minutes in the Ponceau S solution prepared according to the manufacturers instructions and subsequently rinsed with water until red coloured bands appear. The standard proteins are marked with a pencil.

Afterwards the blot is incubated for 30 min in a solution of 0.5% casein in TBS (50 mmol/l Tris HCl, pH 7.5, 150 mmol/l NaCl), in which 20 ml of the reagent is used for 50 to 100 cm². In this incubation the Ponceau S colour disappears again. Afterwards it is washed twice for 10 minutes with 50 ml TBS each and once with 50 ml TBS which in this case contains 1 mmol/l $MgCl_2$, $MnCl_2$ and $CaCl_2$.

A solution is prepared containing lectin conjugated with digoxigenin (preparation according to Example 5) at a concentration of 10 μg/ml in TBS as well as 1 mmol/l each of $MgCl_2$, $MnCl_2$ and $CaCl_2$. The blot is incubated with about 10 ml of this solution for one hour at room temperature. Afterwards it is washed three times with TBS for 10 minutes each.

In order to label the glycoconjugates to be detected the blot is incubated for one hour at room temperature with a dilution of an anti-digoxigenin antibody, which is coupled with alkaline phosphatase, at a dilution of 1:1000 in TBS and afterwards it is washed three times with TBS for 10 minutes each.

In order to visualize the bound label the blot is rinsed for a short time in a solution containing 100 mmol/l Tris-HCl, 100 mmol/l NaCl and 50 mmol/l $MgCl_2$ with a pH of 9.5, and then incubated with a solution containing 10 ml of a solution of 100 mmol/l Tris-HCl, 100 mmol/l NaCl and 50 mmol/l $MgCl_2$ with a pH of 9.5, 37.5 μl X-phosphate (50 mg/ml in dimethyl formamide) and 50 μl nitrotetrazolium blue (NBT) (75 mg/ml in 70% dimethyl formamide). The colour develops after a few minutes. The staining solution is then removed and the blot is rinsed several times in water. The substance to be detected is clearly visible on the blot.

EXAMPLE 8

Glycoprotein detection by blotting with digoxigeninhydrazides

Glycoproteins are oxidized in the dark for 20 minutes at room temperature in 0.1 mol/l sodium acetate buffer, pH 5.5 using 10 mmol/l sodium metaperiodate. Excess sodium metaperiodate is destroyed by addition of sodium bisulphite at a concentration of 20 mmol/l. After 5 minutes digoxigenin-3-carboxymethyl ether-ε-amidocaproic acid-hydrazide-hydrochloride or digoxigenin-O-succinyl-ε-amidocaproic acid-hydrazide-hydrochloride at a concentration of 1 mmol/l is added and the solution is incubated for one hour at room temperature. The glycoproteins thus treated are directly separated by SDS gel electrophoresis and transferred electrophoretically on to nitrocellulose (for example BA85 from Schleicher & Schüll). The nitrocellulose membrane is incubated for at least 30 minutes with 0.5% casein in TBS and after washing several times in TBS it is incubated with a 1:1000 dilution of the anti-digoxigenin antibody which is conjugated with alkaline phosphatase in 10 ml TBS for one hour at room temperature. Afterwards the further procedure is as described in Example 7.

EXAMPLE 7

Glycoprotein Detection by Blotting with Fluoresceinisothiocyanate (FITC)

The procedure is as described in Example 8, whereby instead of digoxigenin hydrazides 1 mmol/l 5-(((2-(carbohydrazino) methyl) thio) acetyl) aminofluorescein (R. P. Hangland, Handbook of Fluorescent Probes and Research Chemicals, Molecular Probes, Inc. U.S.A) is added.

EXAMPLE 10

Glycoprotein Detection in Microtitre Plates (ELISA)

50 μl of the glycoprotein to be detected (protein concentration: 0.1 μg/ml to 0.1 mg/ml in 0.05 mol/l sodium carbonate buffer, pH 9.25) is placed for 30 minutes in a well of a microtitre plate (e.g. NUNC Microwell Plate 96F) for coating. 100 μl 10 mmol/l sodium periodate in 0.1 mol/l sodium acetate, pH 5.5 is added and incubated for 2 minutes at room temperature in darkness. Afterwards it is washed three times with PBS (0.05 mol/l potassium phosphate, pH 6.5, 0.15 mol/l sodium chloride).

100 μl digoxigenin-O-succinyl-ε-amidocaproic acid-hydrazide-hydrochloride or digoxigenin-3-carboxymethyl ether-ε-amidocaproic acid-hydrazide-hydrochloride solution (1 μmol/l in 0.1 mol/l sodium acetate, pH 5.5) is added and incubated for 60 minutes at room temperature. After washing with PBS (three times) it is incubated with 0.3 ml blocking solution [0.5% casein in TBS: 0.05 mol/l Tris-HCl, pH 7.5, 0.15 mol/l sodium chloride] per well for 30 minutes at room temperature. Afterwards it is washed three times with TBS, 0.1% Tween 20.

50 μl antibody solution per well (1 μl anti-digoxigenin antibody, coupled to peroxidase (150 U/ml)) dissolved in 0.5 ml TBS, 0.1% Tween 20, is incubated for 60 minutes at room temperature and washed three times with TBS, 0.1% Tween 20. Afterwards 1.6 mmol/l ABTS (2,2,-azino-di-(3-ethylbenzthiazoline sulphonate) in 95 mmol/l phosphate-citrate buffer, pH 4.4 is added with 3.1 mmol/l sodium perborate, incubated for 30 minutes at room temperature and the absorbance is measured at 405 nm.

Using this method 0.5 ng glycoprotein can clearly be detected per well.

I claim:

1. Method for detecting a carbohydrate containing compound comprising (a) contacting said compound with a conjugate comprising (i) a group which specifically binds to the carbohydrate in said compound and (ii) a hapten having a molecular weight of from 300-1200 to form a complex of said carbohydrate containing compound and conjugate, (b) contacting said complex with a labelled antibody which specifically binds to said hapten, and (c) detecting labelled antibody so as to detect said carbohydrate containing compound.

2. Method of claim 1, wherein said carbohydrate comprises a pentose, a hexose, sialic acid or a derivative thereof and said group specifically binds thereto.

3. Method of claim 1, further comprising oxidizing the carbohydrate of said carbohydrate containing compound prior to contact with said conjugate.

4. Method of claim 1, wherein said carbohydrate containing compound is a sugar.

5. Method of claim 3, comprising oxidizing said carbohydrate with periodate.

6. Method of claim 1, wherein said group specifically binds to said carbohydrate is a lectin.

7. Method of claim 1, wherein said group which specifically binds to said carbohydrate is a functional group which specifically reacts with an aldehyde.

8. Method of claim 4, further comprising oxidizing said sugar with an oxidase prior to contact with said conjugate.

9. Method of claim 7, wherein said functional group is selected from the group consisting of an amine and a hydrazine.

10. Method of claim 1, wherein said conjugate further comprises a spacer of from 3-32 atoms in length, said spacer binding said group which specifically binds to the carbohydrate to said hapten.

11. Method of claim 1, wherein said hapten is selected from the group consisting of digoxin and digoxiginen.

12. Method of claim 1, wherein said labelled antibody is labelled with a member selected from the group consisting of a radioactive label, an enzyme, a fluorescent label, a chemiluminescent label, a bioluminescent label, and gold.

13. Method of claim 12, wherein said enzyme is selected from the group consisting of alkaline phosphatase, peroxidase and $\beta$-galactosidase.

14. Method of claim 1, further comprising electrophoretically separating said carbohydrate containing compound from a sample prior to contact with said conjugate.

15. Method of claim 1, comprising contacting a sample containing said carbohydrate containing compound with said conjugate, and separating conjugate formed therebetween from said sample prior to contact with a labelled antibody.

* * * * *